US011565085B2

United States Patent
Pontecorvo et al.

(10) Patent No.: US 11,565,085 B2
(45) Date of Patent: Jan. 31, 2023

(54) DEVICE FOR ATTACHING A CATHETER

(71) Applicant: Servimed Industrial S.p.A., Rome (IT)

(72) Inventors: Carmine Pontecorvo, Capri (IT); Luca Del Regno, Montoro (IT)

(73) Assignee: SERVIMED INDUSTRIAL S.P.A., Rome (IT)

( * ) Notice: Subject to any disclaimer, the term of this patent is extended or adjusted under 35 U.S.C. 154(b) by 113 days.

(21) Appl. No.: 17/475,800

(22) Filed: Sep. 15, 2021

(65) Prior Publication Data
US 2022/0001143 A1 Jan. 6, 2022

Related U.S. Application Data

(63) Continuation of application No. PCT/IB2020/062160, filed on Dec. 18, 2020.

(51) Int. Cl.
*A61M 25/02* (2006.01)
(52) U.S. Cl.
CPC ....... *A61M 25/02* (2013.01); *A61M 2025/028* (2013.01); *A61M 2025/0213* (2013.01); *A61M 2025/0266* (2013.01)
(58) Field of Classification Search
CPC .......... A61M 25/02; A61M 2025/0213; A61M 2025/0266; A61M 2025/028; A61M 25/0637; A61M 16/0683; A61B 2046/234; A61N 1/37518; A61N 1/0558; A61J 15/0053
See application file for complete search history.

(56) References Cited

U.S. PATENT DOCUMENTS

| | | | |
|---|---|---|---|
| 8,827,960 B2 * | 9/2014 | Haak | D04H 3/011 604/174 |
| 9,220,870 B2 * | 12/2015 | Hyman | A61M 25/02 |
| 2001/0039399 A1 * | 11/2001 | Bierman | A61M 25/02 604/177 |

FOREIGN PATENT DOCUMENTS

WO 2013090903 A1 6/2013

OTHER PUBLICATIONS

International Search Report and Written Opinion for Corresponding International Application No. PCT/IB2020/062160 (11 Pages) (dated Mar. 17, 2021).

* cited by examiner

*Primary Examiner* — Theodore J Stigell
*Assistant Examiner* — Rachel T. Smith
(74) *Attorney, Agent, or Firm* — Lucas & Mercanti, LLP

(57) ABSTRACT

A medical device for fixing a catheter to a patient is disclosed. It includes a base having a planar main development, a first face configured to be glued to a patient's skin, a second face, opposite to the first face, adapted to receive a catheter according to an axis of insertion of the catheter, and at least two pegs which rise substantially perpendicular to the second face. Each peg has a stem which rises from the second face and has a cross section suitable to freely pass through a through hole of a fin of a catheter. The peg also has an enlarged free terminal end having a cross section greater than the cross section of the stem so that it cannot freely pass through the through hole. The enlarged terminal end is able to pass through the through hole only by elastically widening the through hole.

6 Claims, 1 Drawing Sheet

DEVICE FOR ATTACHING A CATHETER

CROSS-REFERENCE TO RELATED APPLICATIONS

This application is a continuation of PCT/IB2020/062160, filed Dec. 18, 2020, which claims the benefit of Italian Patent Application No. 102019000024568, filed Dec. 18, 2019, the contents of each of which are incorporated herein by reference.

The present invention relates to the field of medical devices and in particular relates to an anchoring system for catheters to the body of a patient.

The use of catheters is a common practice in the treatment of patients who require the introduction of fluids, for example intravenous treatments, or the withdrawal of fluids as in the case of bladder catheterization. It is often necessary to use fixation methods that allow the catheter to be kept correctly positioned for the duration of long patient treatments. The most common method involves using medical patches, or adhesive tapes, to cover a portion of the catheter and tighten it to the patient's body.

However, the use of adhesive patches on the patient traditionally involves some drawbacks. Removal can also cause unwanted movement of the catheter over the patient causing pain. Furthermore, repeated application of adhesives to the catheter can lead to the formation of residues on the external surface of the catheter. These residues facilitate accumulation of contaminants that adhere to the catheter itself, increasing likelihood of infection at the insertion site. Another consequence is that the residues can make the catheter more difficult for healthcare professionals to be managed.

The object of the present invention is to provide a fastening device that allows a catheter to be held in the correct position for prolonged times without causing the above mentioned inconveniences.

Another object is to provide a device which is constructively simple and which therefore is economical to use, facilitating its diffusion in health facilities.

These objects are achieved with the catheter fixing device whose essential characteristics are defined by the first appended claim. Other important accessory characteristics are the subject of the dependent claims.

The characteristics and advantages of the catheter fixing device will become clearer from the following description of an embodiment thereof, made by way of non-limiting example with reference to the attached drawings in which.

Figure 1:
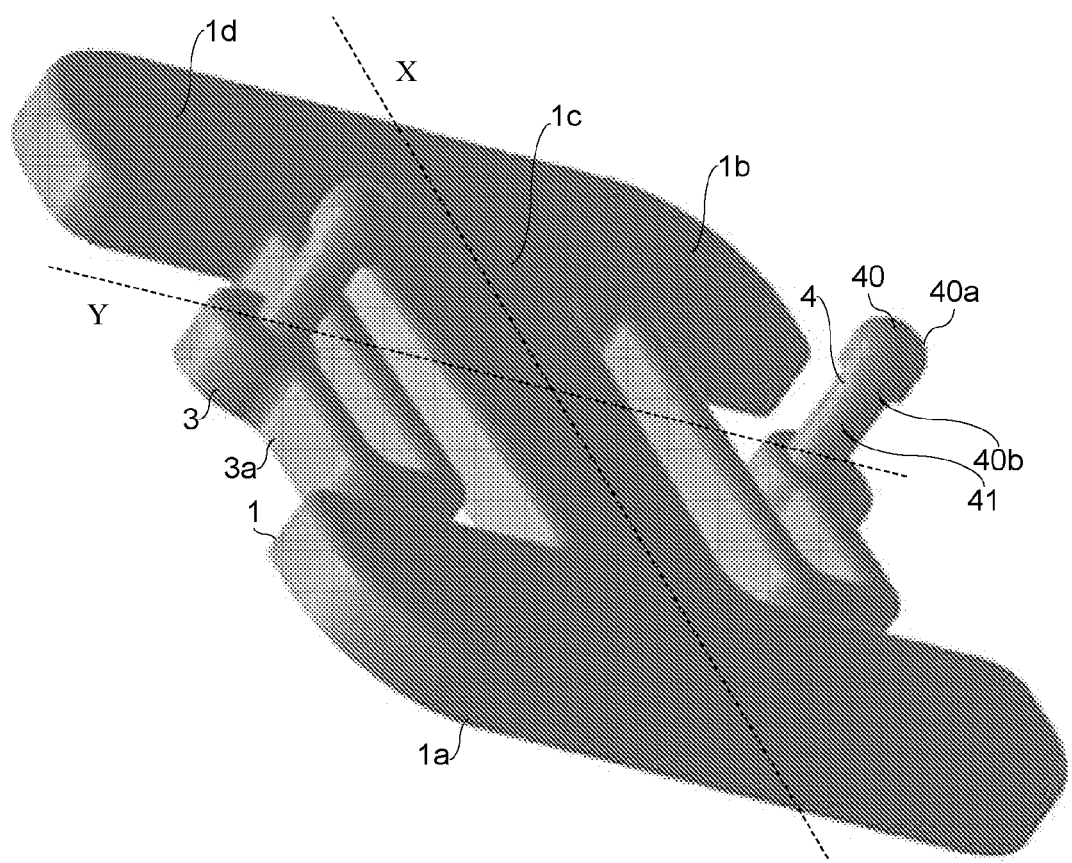
FIG. 1 shows a preferred embodiment of a device fixation for catheters.

With reference to FIG. 1, the fixing device fora catheter according to the present description comprises a base 1. Said base 1 comprises a first face 1a configured to be glued to the skin of a patient by means of the use of adhesive substances applied to the patient's skin and/or to the surface of said first face 1a. Preferably, this first face 1a is coated with an adhesive substance covered by a protective film to preserve its effectiveness. When the base 1 has to be fixed on a patient's skin, the protective film is removed and the base 1 is glued like a common plaster.

According to one aspect, the base 1 has a planar main development.

Figure 2:
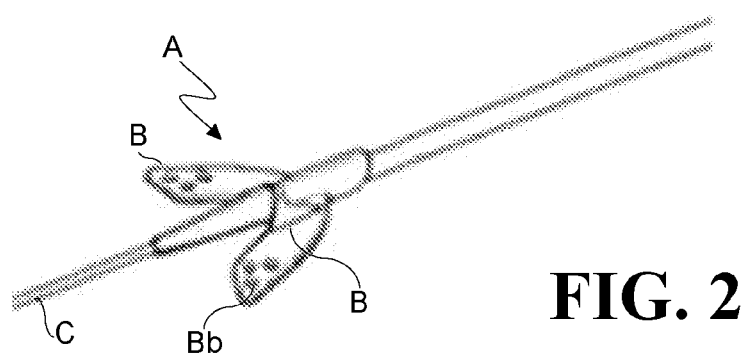
FIG. 2 shows a catheter comprising a fin (not part of the invention).

The base 1 also comprises a second face 1b, facing in the opposite direction to the first face 1a, suitable for receiving and housing a catheter A, shown in FIG. 2 and not part of the invention. The catheter is arranged on the second face 1b defining a first catheter axis X. By way of example only, a catheter shown in FIG. 2 usable with the fixation device of this disclosure can be a central or peripheral venous catheter. Typically, it comprises a needle C adapted to be inserted into the patient's vein and two fins B commonly used to be attached by plasters to the skin of a patient in order to keep the catheter in a correct position. These fins B generally comprise one or more through holes Bb, for each fin, generally used for the application of suture threads. The fins B are generally positioned in a mirror image with respect to the catheter.

The fixing device also comprises two pegs 4 connected to the base 1 which have a main development perpendicular to the second face 1b and are turned outwards with respect to the patient. Furthermore, they are preferably arranged, in a substantially specular way, astride a portion of the second face 1b in order to intercept the fins B of a catheter A. The position from which the pegs 4 rise defines a positioning axis of the pegs Y, perpendicular to the catheter axis X. The pegs 4 comprise a stem 41.

According to one aspect, each stem 41 has a circular cross section with a diameter smaller than the diameter of circular holes Bb of the fins B.

Each peg also comprises an enlarged free terminal end 40 having a cross section greater than the cross section of the respective stem 41 which is in turn configured to be able to be forced to penetrate into the holes Bb of the fins, deforming them elastically. By placing a hole Bb in correspondence with this free end, a user can elastically deform the hole Bb by pressing it against the free end of a peg to allow the insertion of the peg 4 inside the hole. Once the free end has completely crossed the hole Bb, the latter springs back elastically to its original shape around the stem 41. The peg 4 will not be able to spontaneously come out of the hole Bb because the force necessary to make the pegs 4 come out from holes Bb is greater than the forces to which catheters implanted on patients are generally subjected. This feature ensures that the fins B of a catheter, once secured to the pegs 4, are stably associated with the catheter fixation device according to the present description.

According to one aspect, the cross section of the enlarged end 40 of the peg 4 can be about 1.1 to 1.5 times larger than the cross section of the stem 41. According to one aspect, the enlarged end preferably comprises a recess 40a, adapted to facilitate the plastic deformation of hole Bb. The recess 40a comprises a tapering of the terminal portion of the enlarged end 40. Each enlarged end 40 also comprises a joint surface 40b opposite the recess 40a, preferably of an angle substantially of 90°, which connects the end 40 to the stem 41. This joining surface further increases the force necessary to make the pegs 4 come out of the hole Bb.

According to one aspect, the pegs have a substantially circular cross section.

The base 1 has elastically deformable portions 3 on which the pegs 4 are directly fixed. These elastically deformable portions 3 move the pegs along the positioning axis of the pegs Y in response to a stress by the user. The elastically deformable portions 3 mentioned above preferably comprise a connecting segment 3a, thin enough to be flexible.

According to one aspect, a first end of this segment is rigidly connected to a body of the base 1, while a peg 4 is rigidly connected to a second end.

The fact that the pegs are on the elastically deformable portions 3, allows, during the assembly phase of the catheter fins, to first insert only one of the two pegs 4 into a fin of the catheter, after which it is possible to exert a traction, or a push, along the positioning axis of the pegs Y on the fin to bring the peg already inserted at a distance such as to allow the insertion of the second peg 4 inside the second hole Bb on the second fin B. In this way, the fixing device according to the present description can be adapted to the various types of fins B for catheters available on the market, which typically have the holes defined at different mutual distances.

According to one aspect, the base 1 comprises a central portion 1c arranged along the catheter axis X. Two further stabilizing portions 1d are rigidly connected perpendicularly to the ends of this portion, one at each end of the central portion 1c, preferably arranged parallel to the positioning axis of the Y pegs.

According to an aspect illustrated in the figures but not essential for the realization of the device of this disclosure, the three portions are arranged so as to form an "H" shape. However, other embodiments are possible in which the three portions are arranged according to a different geometry.

The first face 1a is defined by the lower face, i.e. the surfaces that come into contact with the patient's skin, of each of the three portions introduced above. Similarly, the second face is defined by the upper faces of the three portions, one central 1c and two stabilizing 1d. Each connection segment 3a is preferably cantilevered connected to a respective stabilization portion 1d, has a development parallel to the catheter axis X and is comprised between said stabilization portions 1d, and is flanked by the central portion 1e. Even more preferably, the connection segment 3a comprises a U-shaped folding on itself so as to increase the possible excursion of the position of the peg along the positioning axis of the pegs Y.

The fastening device is preferably made of flexible plastic material. Even more preferably, the device is a single piece obtained by injection molding or thermoforming.

The procedure to be followed for applying the catheter to a patient's skin by means of the fastener of this disclosure is as follows:

1. Inserting the tip of the catheter into the desired route;
2. Holding the base and the fin, making one of the pegs of the device penetrate into a hole in one of the catheter fins;
3. If necessary, exerting a traction or a push on the fin so as to make a hole in the second fin coincide with the second peg of the device, proceed to make the second peg also penetrate into the hole in the second fin;
4. Preparing the skin for the positioning of the base; and
5. Removing the protective film from the first face of the base, exposing the adhesive substance, and place the first face on the patient's skin.

The fastening device according to the present description has the advantage of allowing the fins of a catheter to be fixed in a stable and safe manner without having to resort to adhesive plasters or tapes. In particular, the enlarged end of the pegs allows a secure coupling between the fins of a catheter and the fixing device.

Thanks to the elastic connection means it is advantageously possible to use the fastening device described in the description with various types of fins available on the market.

Another advantage of the device consists in being extremely simple in construction, since it can be made in a single piece by molding plastic material, while having all the safety and practicality features already described.

The present invention has been described up to now with reference to its preferred embodiments. It is to be understood that other embodiments may exist which pertain to the same inventive core, all falling within the scope of protection of the claims hereinbelow.

The invention claimed is:

1. A device for attaching a catheter to a patient, comprising:
   a base, having a first face configured to be glued to a skin of the patient, a second face opposite to the first face suitable for receiving the catheter according to a catheter insertion axis X; and
   at least two pegs which rise substantially perpendicular to said second face, each peg of said at least two pegs comprising a stem which rises from said second face and which has a cross section dimensioned so as the stem can freely pass through a through hole of a fin of the catheter to be used together with said device, each peg of the at least two pegs further comprising an enlarged free end having a cross section greater than the cross section of the stem and such that the enlarged free end cannot freely cross said through hole, said enlarged free end being configured to cross said through hole only by elastically widening the through hole;
   wherein said at least two pegs are arranged in a substantially symmetrical position with respect to the catheter insertion axis X, defining an axis of pegs' positioning Y, perpendicular to the catheter insertion axis X;
   wherein the at least two pegs are connected to respective elastically deformable portions of said base, said elastically deformable portions being configured to move the at least two pegs along the axis of pegs' positioning Y in response to a force exerted by a user;
   wherein each of said elastically deformable portions comprises a connection segment substantially coplanar with a body of said base, said connection segment being configured to be elastically movable with respect to the axis of pegs' positioning Y, a first end of said connection segment being rigidly connected to said base, a second end of said connection segment opposite to said first end of the connection segment being rigidly connected to a peg of said at least two pegs.

2. The device according to claim 1, wherein the body of said base comprises a central portion, arranged along the catheter insertion axis X, and two stabilization portions rigidly connected to opposite ends of said central portion and oriented transversely to the catheter insertion axis X.

3. The device according to claim 2, wherein each connection segment is cantilevered to a respective one of said stabilization portions and is folded back on itself in a "U" shape.

4. The device according to claim 1, wherein said first face is coated with an adhesive substance covered by a removable protective film that may be removed when said base must be glued on the skin.

5. The device according to claim 1, wherein said base is made of flexible plastic material.

6. The device according to claim 5, wherein said device is a single piece obtained by means of an injection molding or a thermoforming operation.

* * * * *

UNITED STATES PATENT AND TRADEMARK OFFICE
CERTIFICATE OF CORRECTION

| | | |
|---|---|---|
| PATENT NO. | : 11,565,085 B2 | |
| APPLICATION NO. | : 17/475800 | |
| DATED | : January 31, 2023 | |
| INVENTOR(S) | : Carmine Pontecorvo et al. | |

It is certified that error appears in the above-identified patent and that said Letters Patent is hereby corrected as shown below:

On the Title Page

Insert:
--Foreign Application Priority Data
December 18, 2019     (IT)...................102019000024568--

Signed and Sealed this
Seventh Day of March, 2023

Katherine Kelly Vidal
*Director of the United States Patent and Trademark Office*